United States Patent

Rosenthal

Patent Number: 6,006,659
Date of Patent: Dec. 28, 1999

[54] PERSONAL PASTEURIZATION SYSTEM

[76] Inventor: Richard A. Rosenthal, 2680 Pacer La., San Jose, Calif. 95111

[21] Appl. No.: 09/170,698

[22] Filed: Oct. 13, 1998

[51] Int. Cl.$^6$ ..................................................... A61L 2/10
[52] U.S. Cl. .......................... 99/451; 422/24; 250/455.11
[58] Field of Search ............................... 99/451, DIG. 14, 99/483, 453, 452; 422/24; 250/455.11, 435, 436, 438

[56] References Cited

U.S. PATENT DOCUMENTS

| | | | |
|---|---|---|---|
| 5,069,782 | 12/1991 | Moyher, Jr. et al. | 422/24 X |
| 5,653,877 | 8/1997 | Mark | 250/436 X |
| 5,820,821 | 10/1998 | Kawagoe et al. | 250/455.11 X |

Primary Examiner—Reginald L. Alexander
Attorney, Agent, or Firm—Walter A. Hackler

[57] ABSTRACT

An apparatus for cold pasteurization of food products sized and adapted for domestic use, is provided. The apparatus includes a housing, a source of ultraviolet radiation disposed within the housing and having germicidal wavelengths, and a rotatable basket for containing a food product and exposing the product to the source of ultraviolet radiation in order to inactivate pathogens on the food product. A mistifier is provided for directing an aqueous rinse into the basket and onto the food product in order to prevent degradation of organoleptic qualities of the product which may be caused by the ultraviolet treatment. The aqueous rinse may be tap water and the water directed onto the source of ultraviolet radiation in order to sterilize the tap water. An outlet is provided for dispensing the sterilized water for consumption.

21 Claims, 2 Drawing Sheets

PERSONAL PASTEURIZATION SYSTEM

The present invention generally relates to apparatus for cold pasteurization of food products, and more specifically relates to a personal pasteurization system, sized and adapted for use as an ordinary kitchen appliance, for sanitizing foods and water using ultraviolet light.

Sanitation of foods and water for safe human consumption is becoming an increasingly urgent concern as new, more resilient strains of food and water borne pathogens have been proliferating. For example, a bacterial organism known as *E. coli* is ordinarily a benign organism found in the intestines of animals, and on the exterior of plants. However, *E. coli* has the ability to mutate into strains that are highly toxic if ingested. A recently discovered and particularly dangerous strain of the bacteria, called *E. coli* 0157:H7, has been implicated in numerous disease outbreaks, as many as thirty each year across the United States during the past five years. People have been infected and hospitalized as a result of eating contaminated beef, cheese and fresh fruits. In one such outbreak in recent history, it was not contaminated foods, but contaminated tap water that caused an epidemic of seriously ill people across thirteen states. Unfortunately, many experts believe that the problem is on the rise.

As epidemiologists search for answers on how to discover sources of contamination during an epidemic, and as doctors search for new effective treatments, it is believed that prevention and controlling the spread of these pathogens is still the best way to protect the public health.

Treatment of food products using high frequency radiation is considered "cold pasteurization" because it theoretically will not cause significant heating of the food being treated. Irradiation processing using the actinic effects of ultraviolet light has been studied as a possible tool for sterilizing food products by exposing food products, such as bakery items to ultraviolet light at germicidal wavelengths, typically being wavelengths shorter than 300 nanometers. Unfortunately, undesirable superficial effects result from ultraviolet radiation processing of foods, including the development of oxidative flavors and aromas and a change in surface texture.

U.S. patent application Ser. No. 09/002,067 for An Actinic Process and Apparatus for Cold Pasteurization of Fresh Foods and Beverages, which is incorporated herein by this specific reference thereto, discloses an apparatus and process for sanitizing fresh foods and beverage products using multiple stages of exposure to different wavelengths of ultraviolet and infrared light in order to eliminate undesirable microorganisms without altering the nutritional or organoleptic qualities of the product. The apparatus and method disclosed in this referenced patent application represents an important advance in pasteurization of food products in an industrial setting.

However, prior to the development of the present invention, there has been no known apparatus or device developed directed at using ultraviolet light for pasteurization of food and sterilization of water for personal use in a domestic setting. The present invention provides an inexpensive kitchen appliance useful for pasteurizing food products and water using cold pasteurization techniques.

SUMMARY OF THE INVENTION

Accordingly, a personal pasteurization apparatus is provided for enabling a consumer to pasteurize food products and sterilize water in the home, office or even outdoors. The apparatus, in accordance with the present invention, generally comprises a housing sized for accommodation on an ordinary kitchen counter top, and a source of ultraviolet (UV) radiation, having germicidal wavelengths, disposed within the housing. In addition, means, for example a mesh basket, is provided for containing a food product within the housing and exposing the food product to the source of UV radiation.

The housing may be a cylindrical or rectangular enclosure having a volume of preferably less than about 3.0 cubic feet. The source of UV radiation preferably includes two VHO (very high output) mercury vapor lamps affixed to sides of the housing by water tight seals. The mesh basket, or other means for containing the food product, may be rotatable within the housing by means of a small rotisserie motor to thereby optimize exposure of the food product to the UV light.

Importantly, the apparatus also comprises means for directing an atomized aqueous rinse into the basket in order to prevent UV induced damage to organoleptic qualities of the food product. The aqueous rinse preferably comprises water and the means for directing the water may include a high pressure water mistifier. The water is directed into the basket containing the UV irradiated food product as well as directly onto the source of UV radiation to thereby sterilize the water. Means are provided for dispensing the sterilized water for consumption and domestic use.

As will be described hereinafter in greater detail, exposure of food products to the UV radiation will cause inactivation of pathogens disposed on the surface and subsurface of the food product. Although UV treatment will effectively pasteurize the food products, UV treatment causes the creation of a furanol film on the products. This film may cause a noticeable degradation of organoleptic properties of the food, often manifested as a burnt, hay like aroma and chalky taste. The water mistifier provides means for dissolving the furanol film and restoring the lost organoleptic properties of the food product.

An access door on the housing is provided for enabling a user to place food products into the rotatable mesh basket. Upon the user closing the access door and activating an external switch, a preset pasteurization cycle is initiated, causing rotation of the basket, activation of the UV lamps and operation of the water mistifier. As a safety feature, a pressure sensitive switch, or other suitable means may be provided to terminate system power if the access door is opened prior to completion of a cycle.

BRIEF DESCRIPTION OF THE DRAWING

The present invention will be more clearly understood with respect to the following detailed description when considered with the accompanying Drawings of which.

DETAILED DESCRIPTION

Figure 1:
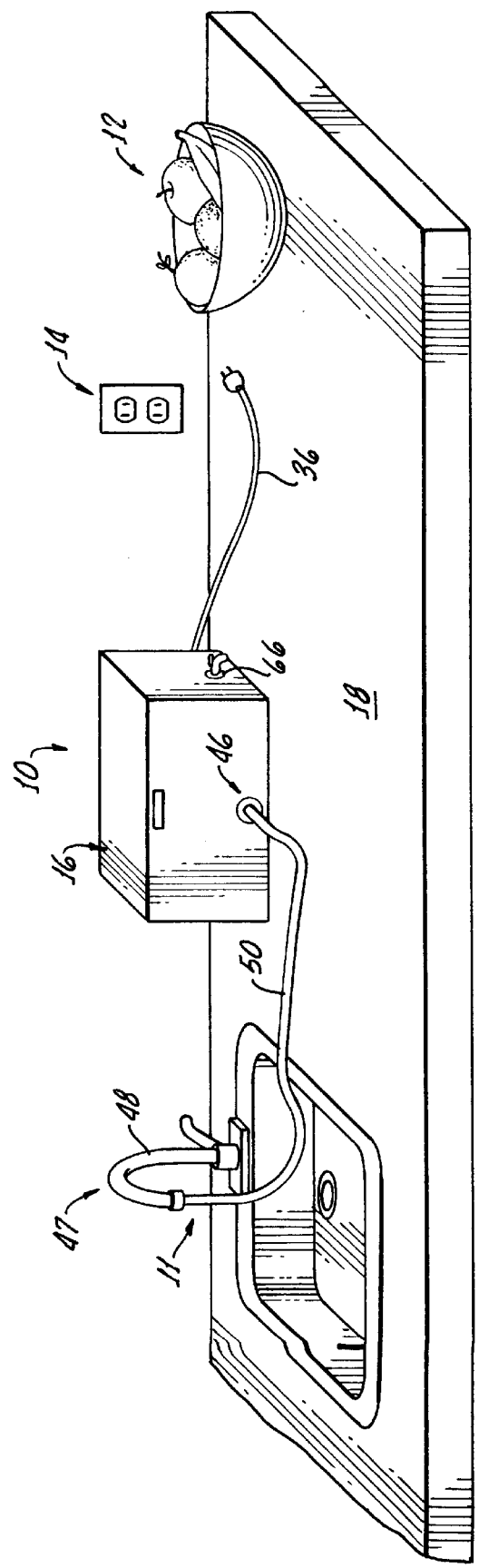
FIG. 1 shows a cold pasteurization apparatus disposed on an ordinary kitchen counter top, the apparatus being sized and adapted for household use.

Turning now to FIG. 1, in accordance with the present invention, a personal pasteurization apparatus 10 for sanitizing water 11 and cold pasteurizing food products 12, is shown. The apparatus 10 is suitable for use with a conventional 110 volt power source, such as that provided by a domestic wall socket 14.

The pasteurization apparatus 10 generally includes a housing 16 sized for accommodation on an ordinary kitchen counter top 18. More particularly, the housing 16 may be a cylindrical or rectangular enclosure having a volume of less than about 3.0 cubic feet. The housing 16 is preferably made of stainless steel or other suitable material that will be attractive to view and easy to clean.

Figure 2:
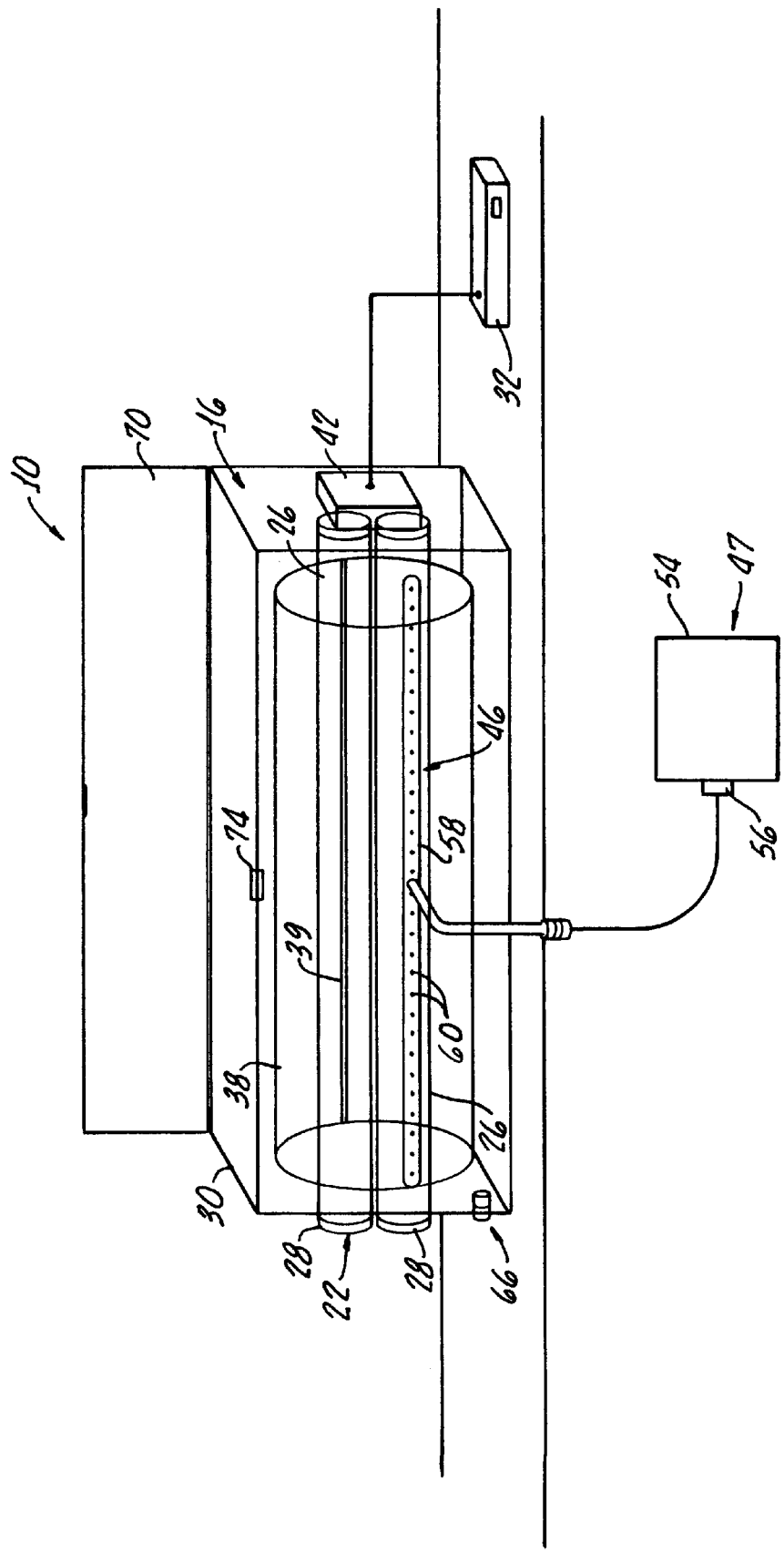
FIG. 2 shows a perspective representation of the cold pasteurization apparatus shown in FIG. 1.

FIG. 2 shows a perspective representation of the personal pasteurization apparatus 10. As shown, the apparatus 10 further comprises, disposed within the housing 16, a source 22 of LW radiation having germicidal wavelengths.

It is known that high intensity ultraviolet radiation may be used for sterilization by abating growth of undesirable microorganisms such as viruses, bacteria, spores, yeasts, molds and protozoa. A general familiarity of the interaction of light with molecules in a living microorganism is necessary to an understanding of the present invention. Ultraviolet light is actinic in that it can produce chemical changes in an organism. The energy absorbed by a molecule radiated with ultraviolet radiation corresponds to the amount of energy necessary to excite electrons from the highest occupied molecular orbital (ground state) of lowest energy to the lowest occupied molecular orbital (excited state) of highest energy. Light absorbing molecules in a microorganism, called chromophores, absorb photons of ultraviolet radiation after transferring their electromagnetic energy to the chemical energy of the molecule in the excited state.

These chromophores are subsequently converted to photoproducts by two major photochemical reactions known as "photoaddition" and "photoisomerization" which will now be briefly discussed in turn. The reaction of an excited state molecule to form a covalently linked photoproduct is sometime referred to as a "photoaddition reaction" and correspondingly, the products of such reaction are referred to as "photoadducts". Photoadducts include cyclobutane thymine dimers and pyrimidine (6-4) pyrimidone dimers. A reaction sometimes referred to as a "photoisomerization reaction" occurs in molecules containing at least one carbon-carbon double bond ("C=C") that is not a ring structure. The prefixes "cis" and "trans" designate two arrangements of substituents that are attached to the C=C double bond and the two structures may be referred to as "cisisomers" and "trans-isomers" respectively. Photoisomerization occurs when one of these isomers is converted to the other.

During ultraviolet radiation treatment, these two photochemical reactions disrupt the basic structural integrity of a microorganism by a tertiary, i.e. three-dimensional, structural rearrangement of the microorganism's proteins and enzymes. This disruption renders the microorganism unable to replicate itself or transport and metabolize nutrients essential for survival. Thus, the pathogens become inactivated by the UV radiation.

In order to produce a germicidal effect, the ultraviolet radiation preferably has a wavelength of between about 220 nm to about 310 nm. The source 22 of ultraviolet radiation may comprise at least one, and preferably two, very high output (VHO), low pressure and low temperature mercury vapor lamps 26 affixed by two water tight seals 28 at each end 30 of the housing 16. The lamps 26 may be powered by any suitable means, for example, utilizing a 115 volt AC ballast 32 connected to the power source 14 by means of a conventional plug 36 (see FIG. 1). Alternatively, solar power provided by, for example a 12 volt solar power source, may be utilized.

The apparatus 10 further comprises means, such as a stainless steel mesh basket 38, disposed within the housing for containing the food product (not shown in FIG. 2 for the sake of simplicity) and exposing the food product to the source 22 of UV radiation. The mesh basket 38 may be cylindrical in shape, and including a latchable door 39 for allowing a user to place food products therein. The mesh basket 38 may be disposed about one inch apart from the UV lamps 26. Food products which may be treated by the apparatus of the present invention include, but are not limited to, fresh fruits and vegetables, prepared or raw meat items, and some bakery items. In use, items are preferably packed loosely in the basket to ensure optimal exposure to the UV light.

Preferably, means, such as a small rotisserie motor 42 is provided for rotating the basket 38, and causing tumbling of food products placed therein, in order to optimize exposure of the food product to the source 22 of UV radiation. The motor 42 may be connected to the ballast 32.

In order to prevent UV induced degradation of the organoleptic qualities of the food product, the apparatus 10 additionally includes means, for example a high pressure water mistifier 46 for directing an aqueous rinse, such as tap water, onto the food products. The water mistifier 46 may be connected to a water source 47, such as a kitchen faucet 48 by any suitable plumbing connector 50, as shown in FIG. 1. Alternatively, as represented in FIG. 2, the water source 47 may comprise a reservoir 54 and pump 56 for supplying water, or beverage products as will be discussed hereinafter, to the mistifier 46.

Ultraviolet radiation treatment of the food product results in the creation of a furanol film (not shown) on the surfaces of the product. This furanol film is a by-product of the breakdown of phelonics by reactive oxygen species into intermediate hydroquinoines which are subsequently degraded into furans. The furanol film degrades the organoleptic properties of the food product resulting in a burnt, hay-like aroma and chalky taste. The water mistifier 46 provides means for dissolving the furanol film, restoring the organoleptic properties of the food product.

Another feature of the present invention is the sterilization of water for destruction of E. coli and other microorganisms that may have contaminated the water supply. This is provided by introducing, or directing, the water mistifier onto the UV radiation source 22. As shown in FIG. 2, the water mistifier may include an atomizer or spray bar 58 including outlets 60 directed at both the lamps 26 and the mesh basket 38. Upon contact with the activated lamps 26, the water is effectively sterilized.

Accordingly, the apparatus may further comprise an outlet 66 (see also FIG. 1) for dispensing the sterilized water for drinking, cooking, or other domestic use. Advantageously, therefor, the present invention provides a means for cold pasteurizing water, such as tap water.

It should be appreciated that in addition to sterilization of water, with appropriate modification to the water mistifier 46, the present invention may be used to pasteurize liquid food products such as clear juices by filling the reservoir with the liquid product and directing the liquid product onto the UV radiation source 22.

An access door 70 on the housing 16 is provided for enabling a user to place food products into the rotatable mesh basket 38 to begin the sterilization process. The door 70 also provides means for removing the irradiated and rinsed food product from the housing 16.

In addition, a preset sterilization cycle may be electronically programmed into the apparatus 10 for facilitating use. The preset sterilization cycle may be initiated only after the access door 70 has been securely closed. A full sterilization cycle may include a timed activation of the UV lamps 26 for destroying organisms on the surface of the food products, introduction of the aqueous rinse into the basket 38 and onto the lamps 26 while the lamps 26 are activated, in order to dissolve the furanol film and sterilize water if desired, and rotation of the basket 26 during the full cycle. For example, an effective period of time for sterilization of 1.5 gallons of water may be as long as three minutes, while typically about one minute is required to pasteurize food products for Log 2 to Log 3 reduction of microbial pathogens. A pressure sensitive switch 74, or other suitable component, may be provided for terminating power to the apparatus if the access door 70 is opened prior to completion of the full cycle.

A method for cold pasteurizing food products and sterilizing water is also provided by the present invention. The method may comprise the steps of providing the housing 16 hereinabove described, containing a food product within the housing 16 rotating the food product contained within the housing 16 radiating actinic light at the rotating food product, from the UV light source, disposed within the housing 16, in order to inactivate pathogens on the food product, and directing a water rinse onto the UV light source 22 onto the irradiated food product in order to sanitize the water and prevent UV induced degradation of the food product.

It is to be appreciated that the convenient size and low power requirements of the present invention enable pasteurization and sterilization not only in the home and office, but also during travel. For travelers, the personal pasteurization apparatus 10 is easily transported and may be quickly installed in a hotel room for example.

In addition, the personal pasteurization apparatus 10 may be used outdoors or in other situations where plumbing and electrical power may not be readily available. For outdoor use, the apparatus 10 may be designed to be completely self-contained. More particularly, the water source 47 may be provided by the reservoir 54 and pump 56 arrangement such that the reservoir 54 may be filled with water from a stream or lake. In addition, power to the lamps 26 and motor 42 may be provided by a conventional solar power arrangement.

Although there has been hereinabove described a household pasteurization system, in accordance with the invention, for the purpose of illustrating the manner in which the invention may be used to advantage, it will be appreciated that the invention is not limited thereto. Accordingly, any and all modifications, variations, or equivalent arrangements which may occur to those skilled in the art should be considered to be within the scope of the invention as defined in the appended claims.

What is claimed is:

1. Personal pasteurization apparatus suitable for use with a conventional 110 volt power source, the apparatus comprising:
    a housing sized for accommodation on a kitchen counter top;
    a source of UV radiation having germicidal wavelengths, disposed within the housing;
    means for containing a food product within the housing and exposing the food product to the source of UV radiation in order to inactivate pathogens on the food product; and means, disposed within the housing, for directing water onto the source of UV light and into the means for containing the food product in order to sanitize the water and prevent UV induced damage to the food product.

2. The personal pasteurization apparatus according to claim 1 wherein the housing has a volume of less than about 3.0 cubic feet.

3. The personal pasteurization apparatus according to claim 1 further comprising means for rotating the food product in order to optimize the exposure of the food product to the source of UV radiation.

4. The personal pasteurization apparatus according to claim 1 wherein the means for directing water comprises a water mistifier.

5. The personal pasteurization apparatus according to claim 1 further comprising outlet means for dispensing the sanitized water.

6. The personal pasteurization apparatus according to claim 1 wherein the UV radiation has a wavelength of between about 220 nm and about 310 nm.

7. The personal pasteurization apparatus according to claim 6 wherein the source of UV radiation comprises at least one mercury vapor lamp.

8. Cold pasteurization apparatus comprising:
    a housing;
    means, disposed within the housing and including a source of UV radiation, for inactivating undesirable microorganisms on a food product, the UV radiation causing a furanol film on the food product;
    means, disposed within the housing, for containing and exposing the food product to the source of UV radiation; and
    means, disposed within the housing, for preventing UV induced degradation of the food product, including means for dissolving the furanol film caused by the UV radiation on the food product.

9. The cold pasteurization apparatus according to claim 8 wherein the means for dissolving the furanol film includes means for introducing an aqueous rinse onto the food product.

10. The cold pasteurization apparatus according to claim 8 wherein the means for dissolving the furanol film includes means for introducing an aqueous rinse onto the food product and onto the source of UV radiation.

11. The cold pasteurization apparatus according to claim 9 wherein the means for introducing an aqueous rinse comprises a water mistifier.

12. The cold pasteurization apparatus according to claim 8 wherein the means for containing and exposing the food product includes means for rotating the food product in order to optimize the exposure of the food product to the source of UV radiation.

13. The cold pasteurization apparatus according to claim 8 wherein the UV radiation has a wavelength of between about 220 nm and about 310 nm.

14. The cold pasteurization apparatus according to claim 13 wherein the source of UV radiation comprises at least one mercury vapor lamp.

15. The cold pasteurization apparatus according to claim 8 wherein the housing is sized for accommodation on a kitchen counter top.

16. The cold pasteurization apparatus according to claim 15 wherein the housing has a volume of less than about 3.0 cubic feet.

17. Personal pasteurization apparatus suitable for use with a conventional 110 volt or 12 volt solar power source, the apparatus comprising:
    a housing sized for accommodation on a kitchen counter top;
    a source of UV radiation having germicidal wavelengths, said source of UV radiation including at least one mercury vapor lamp sealed within the housing;
    basket means for containing a food product within the housing and exposing the food product to the source of UV radiation in order to inactivate pathogens on the food product;

means, including a rotisserie motor, for rotating the basket means;

means, disposed within the housing, for directing water onto the source of UV light and into the basket means in order to sanitize the water and prevent UV induced damage to the food product; and outlet means for dispensing the sanitized water.

18. The personal pasteurization apparatus according to claim 17 wherein the at least one mercury vapor lamp comprises two mercury vapor lamps.

19. The personal pasteurization apparatus according to claim 18 further comprising means, including a 115 volt AC ballast, for powering the two mercury vapor lamps and the rotisserie motor.

20. The personal pasteurization apparatus according to claim 17 wherein the housing has a volume of less than about 3.0 cubic feet.

21. A method for cold pasteurizing food products and sterilizing water, said method comprising:

providing a housing sized for accommodation on a kitchen counter top;

containing a food product within the housing;

rotating the food product contained within the housing;

radiating actinic light at the rotating food product, from a UV light source within the housing, in order to inactivate pathogens on the food product;

directing a water rinse onto the UV light source onto the irradiated food product in order to sanitize the water and prevent UV induced degradation of the food product;

providing a means for removing the irradiated and rinsed food product from the housing; and providing a means for dispensing the sanitized water for consumption and domestic use.

* * * * *